United States Patent [19]

Milligan et al.

[11] 3,933,594
[45] Jan. 20, 1976

[54] METHOD AND DEVICE FOR DETERMINING THE CONCENTRATION OF A SUBSTANCE IN A FLUID

[75] Inventors: Terry W. Milligan, Belmont; Richard F. Wright, Acton, both of Mass.

[73] Assignee: Polaroid Corporation, Cambridge, Mass.

[22] Filed: Aug. 16, 1974

[21] Appl. No.: 498,022

[52] U.S. Cl. .................. 195/103.5 R; 195/103.5 C
[51] Int. Cl.² ......................................... G01N 31/14
[58] Field of Search ............. 195/103.5 R, 103.5 C; 23/253 TP

[56] References Cited
UNITED STATES PATENTS

| | | | |
|---|---|---|---|
| 3,690,836 | 9/1972 | Buissiere et al. | 195/103.5 R X |
| 3,723,064 | 3/1973 | Liatta | 23/253 TP |
| 3,783,105 | 1/1974 | Moyer et al. | 23/253 TP |
| 3,785,930 | 1/1974 | Ellis | 195/103.5 R X |
| 3,791,933 | 2/1974 | Moyer et al. | 23/253 TP |

*Primary Examiner*—A. Louis Monacell
*Assistant Examiner*—Esther L. Massung
*Attorney, Agent, or Firm*—Philip G. Kiely

[57] ABSTRACT

A diagnostic test device comprising a first and second sheet attached at a leading edge; an absorbent medium intermediate said first and second sheet in spaced relationship to said sheets. The fluid containing the substance to be analyzed is placed on the absorbent medium. Compressive force would then be applied to the test device to remove excess fluid from the absorbent medium and to bring the fluid into contact with the first and second sheets which contain reagents adapted to react with the substance to provide a colorimetric determination of the presence and/or concentration of the substance.

10 Claims, 4 Drawing Figures

METHOD AND DEVICE FOR DETERMINING THE CONCENTRATION OF A SUBSTANCE IN A FLUID

BACKGROUND OF THE INVENTION

A variety of devices are known today for analysis of body fluids such as urine, blood, etc. Such devices generally employ extremely accurate procedures and provide a valuable diagnostic tool. However, most such devices are expensive, require trained personnel and involve time-consuming techniques. Obviously, such devices are unavailable for use by a layman in, for example, daily monitoring of a diabetic condition.

To fill this very important need a number of relatively simple devices and test strips have been developed and marketed. Many of the so-called simple devices developed for use by untrained personnel suffer from a variety of deficiencies. Accuracy, the ability of the operator to discern relatively minor changes and ease of use are some of the problems encountered with such prior art devices.

It is an object of the present invention to provide techniques and devices not susceptible to the deficiencies of the prior art.

SUMMARY OF THE PRESENT INVENTION

The present invention is directed to a relatively simple diagnostic test device for use in analyzing a substance contained in a body fluid. In accordance with the present invention, a fluid, such as urine, containing the substance to be analyzed, is placed in an absorbent medium which is located between two sheets, but initially spaced apart and out of contact with the sheets. The absorbent medium is selected to carry a predetermined amount of fluid, and any excess is removed by the application of a compressive force which also brings the absorbent medium and the fluid it contains into contact with the aforementioned sheets. While the three elements of the device are maintained in superposed relationship, the substance in the fluid reacts with reagents retained on one or both of the sheets, at least one of which is transparent.

The reaction provides a visual determination (observed through the transparent sheet) of the qualitative and/or quantitative presence of the substance.

DETAILED DESCRIPTION OF THE INVENTION

Figure 1:
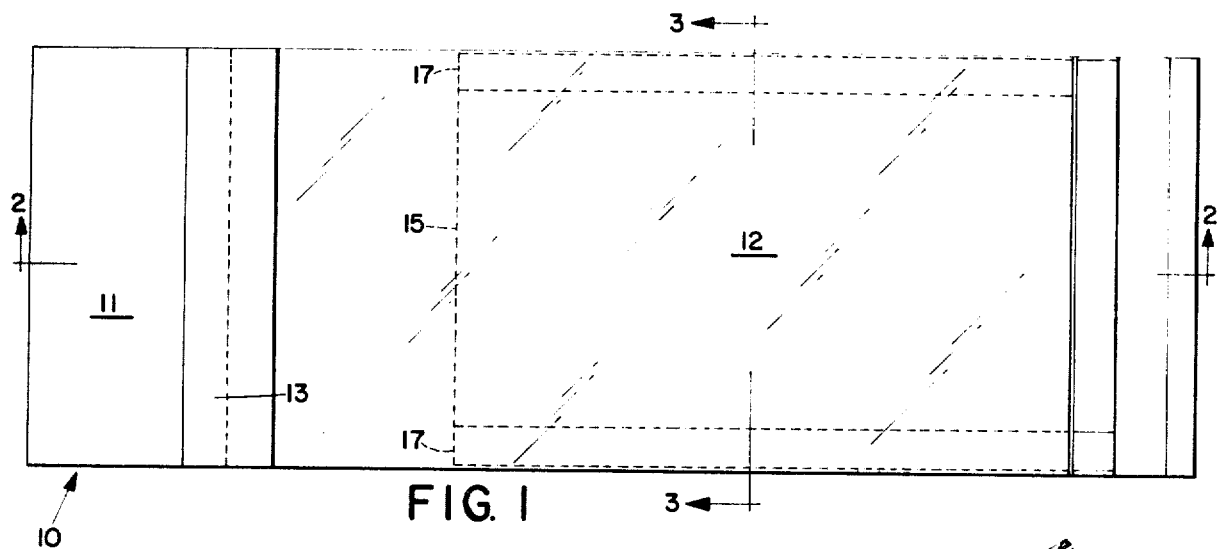
FIG. 1 is a top view of the testing device of the present invention.
Figure 2:
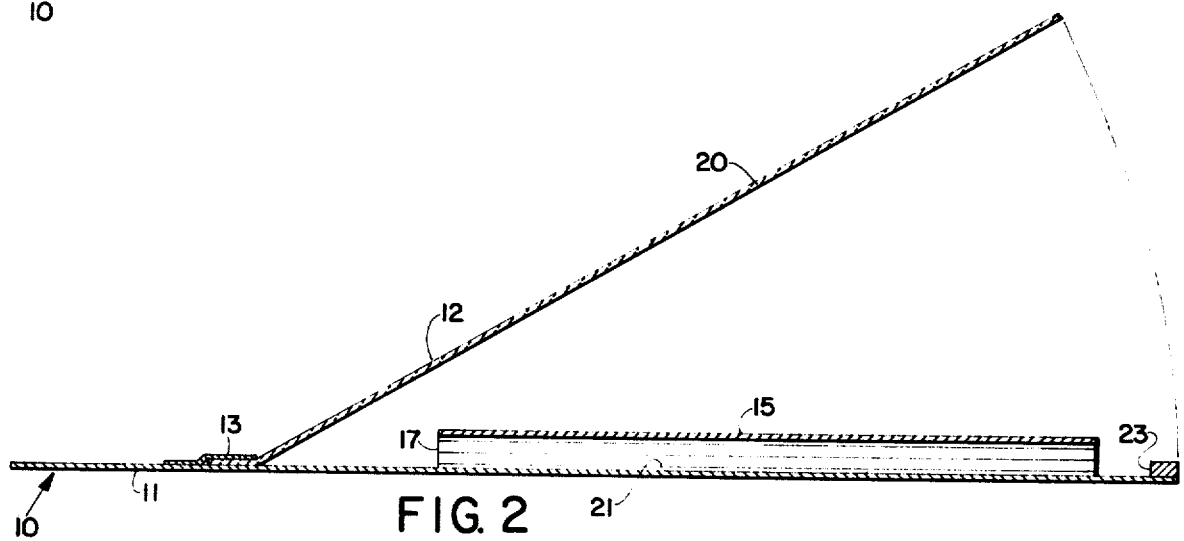
FIG. 2 is an enlarged cross-sectional view of the device of FIG. 1 taken along the line 2—2.
Figure 3:
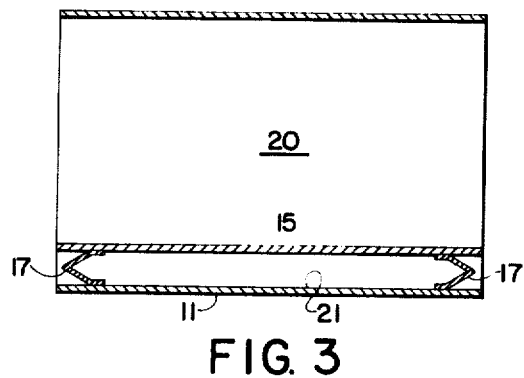
FIG. 3 is transverse sectional end view of the device of FIG. 1 taken along line 3—3.

The present invention is directed to a method and a device useful in said method for qualitative and/or quantitative determination of substances, particularly substances in body fluids. Thus, by means of the present invention, analysis of substances in blood, urine, etc., can be carried out quickly and easily without the need of trained personnel to provide an accurate measure of the substance under consideration in a body fluid.

The novel device of the present invention comprises an absorbing, fluid receiving medium initially located between, but not in contact with, two sheets. At least one sheet is transparent and at least one sheet has a suitable indicator or reagent retained on the inner surface to provide the determination of the substance under test. Fluid is applied to the absorbing fluid receiving medium and the device is then subjected to a compressive force squeezing out excess fluid from the absorbing medium and placing the two sheets in contact with the absorbing medium. The substance reacts with the reagents disposed on one or more of the sheets, providing a visual determination of the substance. The visual determination, generally a colorimetric determination, is viewed through the transparent sheet and compared against a standard scale, either attached to the test device or separate therefrom. By matching the color of the test device with the scale an accurate determination is readily available. The test device may then be discarded. Since a measured amount of fluid is contacted with a premeasured amount of reactants, a quantitative determination is achieved.

To describe the operation of the diagnostic test device in more detail, the operator will lift at least a portion of one of the two sheets exposing the absorbent, fluid receiving medium. To permit access to the fluid receiving medium, it is preferred that the two sheets be joined only at or near the leading edges. To avoid leakage from the sides during application of the compressive force, an adhesive may be employed along the open edges and end of the sheets which is activated by the application of compressive force.

The absorbent fluid receiving medium is located intermediate the sheets in spaced apart relationship. Preferably, the absorbent medium is disposed on support members mounted on one sheet which are deformable under force to permit contact between the sheets and the absorbent medium.

Upon exposing the fluid receiving medium, the operator will place the fluid containing the substance to be tested on the absorbent material. It is not necessary to apply a measured amount of fluid; it is only necessary that the absorbent material be saturated. Subsequent operation of the fluid test device will accurately measure the amount of fluid to be contacted with the reagents.

The device is then moved relative to and between a pair of juxtaposed members or, alternatively, rollers are moved relative to the device. These members may comprise a pair of substantially parallel rollers, a roller and a plate or any other apparatus that will, as the device is moved through it, force the excess fluid from the absorbent medium. By maintaining a specific gap between the juxtaposed pressure-applying members, excess fluid will be discharged from the absorbent medium with an accurate amount retained in the test area between the sheets containing the reagents. The gap between the pressure-applying members would be a function of the thickness of the absorbent medium and the volume of the fluid a function of the thickness and porosity of the absorbent medium.

By extending the length of the sheets beyond the test area sufficiently no excess will spill out the end. Alternatively, absorbent trap means may be provided at the trailing end of the sheets to take care of any excess.

To avoid spillage along the edges of the sheets adjacent the absorbent medium, the test area may be sealed if desired. Sealing will occur during application of pressure during movement through the juxtaposed members, employing a pressure sensitive adhesive, a Velcro fastener, or a fluid actuated adhesive, such adhesive means preferably located along the marginal edge portions. In still another embodiment, the edges may contain spacing means or rails to more accurately control the space between the sheets in the test area, thereby controlling the quantity of fluid. The aforementioned adhesive means may be associated with the spacing means.

The support means which maintains the absorbent material out of contact with the sheets prior to the application of the compressive force may comprise any suitable support which possesses sufficient rigidity to maintain the absorbent material in spaced apart relationship from the sheet, but which will deform, compress or fold to permit contact upon the application of compressive force. Polymeric foams and bifolded materials such as plastic or paper may be employed.

The test reagents which are adapted to react with the substance being tested for are disposed intermediate the two sheets either by coating directly on the sheets or by incorporating them into a suitable carrier or binder material.

The substance in the fluid undergoes one or more reactions with the reagents which provide a colorimetric determination of the substance in the fluid, which is viewed through the transparent sheet and, if desired, compared with a suitable scale which may comprise a portion of the test device. Preferably, the reactants comprise enzymes and coenzymes and a colorimetric indicator, all of which are well known to the art to utilize known reactions.

Turning now to the drawings, the diagnostic test device 10 of the present invention is composed of first sheet 11 hingedly joined at point 13 to second sheet 12, near the leading edge of sheet 11. Sheet 11 carries, at the edges, bifolded deformable support members 17 which support absorbent means 15. Surface 20 of sheet 12 and surface 21 of sheet 11 retain the necessary reagents and indicators to provide the visual concentration of the substance. The reaction may occur within the absorbent medium 15 when the reagents from the sheets diffuse therein upon solubilizing the fluid. If both sheets are transparent, the color indication will be views by transmission. If one sheet is transparent, the color is viewed by reflection.

Figure 4:
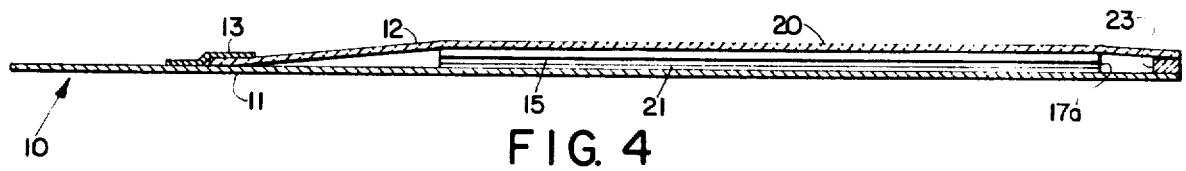
FIG. 4 is an enlarged cross-sectional view of the device of FIG. 1 during operation.

FIG. 4 shows the test device 10 of FIG. 1 after the application of the fluid and the application of the compressive force. Support members 17a are in a collapsed position permitting contact of surfaces 20 and 21 with absorbent medium 15. Trap 23, adapted to retain any excess fluid, is also shown.

The color obtained by the reaction of the reagents and the substance can be compared with a chart containing permanent color gradations calibrated to concentrations of the substance under test. Thus, the operator can immediately and conveniently obtain a numerical determination of the concentration of the substance avoiding delay or any fading or deterioration of the thus-produced colored reaction product.

The adsorbent means may comprise any suitable material adapted to retain fluid and also which will give up the fluid under compressive force. Thus, cloth, sponge, polymeric open cell foams, microporous filters and the like may be employed.

It may be desirable to remove some components of the fluid prior to contacting the fluid with the reactants. Such components may be removed by superposing a filter over the absorbent means to remove the components from the test area. Alternatively, precipitants may be employed in the absorbent means itself. Protein is one example of a component of the fluid that may be removed prior to the reaction.

The sheets which comprise the walls of the device are preferably transparent and may be composed of any suitable material which will retain the reactants without leakage or without interfering with the reaction.

As stated above, the novel device of the present invention may be employed for a variety of diagnostic tests. For example, hemoglobin in blood may be ascertained by application of a blood sample to the absorbent material and disposing an oxidizing agent and a suitable indicator intermediate the superposed sheets. Suitable indicators are known to the art for such a test.

The novel test device of the present invention is particularly suitable for the enzymatic analysis of glucose in body fluids. The test for glucose is based on the following reaction sequence:

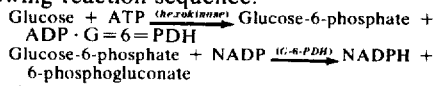

Glucose-6-phosphate + NADP 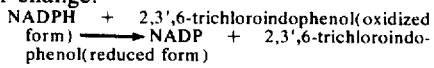 NADPH + 6-phosphogluconate

The absorption of NADPH at 340 nm is a measure of the glucose content in the sample fluid. Since 340 nm is beyond the visible region of the electromagnetic spectrum, a suitable indicator may be included in the system which will react with NADPH to give a suitable color change.

NADPH + 2,3',6-trichloroindophenol(oxidized form) ⟶ NADP + 2,3',6-trichloroindophenol(reduced form)

ATP = Adenosine triphosphate
ADP = Adenosine diphosphate
NADP = Nicotinamide adenine dinucleotide phosphate
NADPH = Nicotinamide adenine dinucleotide phosphate reduced
G-6-PDH = Glucose-6-phosphate dehydrogenase The body fluid containing the glucose would be applied to the absorbent material. The reactants, ADP, NADP and a colorimetric indicator, would be located intermediate the sheets, preferably coated thereon. Suitable indicators include methylene blue, the sodium salt of 3'-chloroindophenol, the sodium salt of 2,3',6-trichloroindophenol and the sodium salt of 2,6-dichloroindophenol. It may be desirable to apply suitable time delay layers, e.g., polymeric layers of specific solubility or permeability, to one or more of the reactants to ensure the order of reaction. The color generated by the reaction will be compared visually with suitable color reference standards.

In a preferred embodiment, the ATP and NADP would be applied to surface 20 of sheet 12 and the colorimetric indicator would be coated on the surface 21 of transparent window 11. The ATP and NADP and/or enzymes may be disposed in the reaction zone just prior to application of the compressive force. However, in a particularly preferred embodiment, the enzymes and/or coenzymes are in a stable, immobilized state which, upon contact with the fluid to be tested, is activated.

In still another embodiment, in addition to the above-mentioned time delay layers, the reactants may be disposed in a suitable polymeric material and a layer of such a material cast on the aforementioned surface.

It is also known to bind enzymes to polymeric matrices. For example, in a cross-linked dextrose gel, adjacent hydroxyl groups can react with cyanogen bromide and then combine with amino groups of the enzyme. Other systems for incorporating enzymes into the matrix of a polymer or other support material are also known.

If the fluid to be analyzed contains a reducing substance (e.g., ascorbic acid in urine), it is preferred to employ a colorimetric indicator system that does not rely on a redox system to avoid any interference in the determination or inaccurate readings. For example, in a glucose determination a suitable indicator system may comprise a ferric salt, such as ferric nitrate coated on silica gel. A ferric-NADH salt is formed which is purple. While the thus-formed colorimetric determination is suitable for the aforementioned glucose determination, if a permanent record of the test is desired then 1,10-phenanthroline or 4,7-diphenyl-1,10-phenanthroline also coated on the silica gel will provide a pink, permanent.

In an alternative embodiment, a mordant for the colored moiety produced in the present invention is employed. This would provide a degree of immobility to the colored species rendering the visual comparison more effective and accurate and still further lessening time of examination as a factor. The use of a mordant would also minimize any reversible reaction which might lead to inaccuracy in the determination. Mordants are well known to the art for a variety of colored materials and the particular mordant will be selected with the particular colored material in mind. Alternatively, an insoluble indicator may be employed.

As stated above, the novel device of the present invention is suitable for use in a variety of diagnostic tests. In the following table, representative substances to be analyzed are indicated with examples of specific enzymes required for the determination.

| Substance | Enzymes |
| --- | --- |
| Glucose | Hexokinase |
|  | Glucose-6-phosphate dehydrogenase |
| Alcohol | Alcohol dehydrogenase |
| Triglycerides | Glycerol kinase |
|  | Pyruvate kinase |
|  | Lactate dehydrogenase |
| Blood urea nitrogen | Urease |
|  | l-glutarate dehydrogenase |
| Aldolase | Triosephosphate isomerase |
|  | Glyceraldehyde-3-phosphate dehydrogenase (GDH) |
| Creatine phosphokinase | Hexokinase |
|  | Glucose-6-phosphate dehydrogenase |
| Glutamate-oxalacetate transaminase | Malate dehydrogenase |

What is claimed is:

1. A device for determining concentrations of a substance in a fluid which comprises:
    a first sheet carrying deformable support members;
    said support members carrying an absorbent fluid receiving medium spaced apart from said first sheet;
    a second sheet pivotally attached at one end to said first sheet and adapted to be superposed over said absorbent fluid receiving means; at least one of said first and second sheets is transparent, and said first sheet carrying one or more reagents; said reagents being present in a predetermined concentration and adapted to react with said substance to provide a visual indication of the concentration of said substance.

2. The device of claim 1 wherein said reagents comprise enzymes, coenzymes and colorimetric indicators.

3. The device of claim 1 wherein said absorbent fluid means comprises a polymeric open cell foam.

4. The device of claim 1 wherein said absorbent fluid means comprises a microporous filter.

5. The device of claim 1 wherein said fluid comprises blood.

6. The device of claim 5 wherein said reagents comprises hexokinase, glucose-6-phosphate dehydrogenase, adenosine triphosphate and nicotinamide adenine dinucleotide phosphate.

7. The device of claim 2 wherein said enzymes and coenzymes are disposed on one of said sheets and said colorimetric indicator is disposed on the other of said sheets.

8. The device of claim 1 wherein one of said transparent sheets includes a colored scale indicating concentration standards for said substance.

9. The device of claim 1 which includes means for removing undesirable components from said fluid prior to contacting said reagents with said fluid.

10. A method for determining the concentration of a substance in a fluid which comprises:
    disposing said fluid onto absorbent fluid receiving means carried on a first sheet by deformable support members in a spaced apart relationship to said sheet;
    superposing a second sheet over said absorbent fluid receiving means; at least one of said first and second sheets is transparent; and
    subjecting said first and second sheets to sufficient compressive force to discharge excess fluid from said absorbent fluid receiving means thereby retaining a predetermined quantity of said fluid in said absorbent fluid receiving means, compressing said deformable members sufficiently to contact said fluid in said absorbent fluid receiving means with a predetermined concentration of reagents; said first sheet carrying one or more of said reagents; said reagents adapted to react with said substance to provide a visual indication of the concentration of said substance.

* * * * *